United States Patent

Rostock et al.

Patent Number: 5,994,347
Date of Patent: Nov. 30, 1999

[54] FOR A PROCESS FOR TREATMENT OF ANXIETY AND TENSION

[75] Inventors: Angelika Rostock; Rita Dost, both of Dresden; Christine Tober, Weinböhla; Reni Bartsch; Klaus Unverferth, both of Dresden; Chris Rundfeldt, Coswig, all of Germany

[73] Assignee: Arzneimittelwerk Dresden GmbH, Germany

[21] Appl. No.: 09/079,802

[22] Filed: May 15, 1998

[51] Int. Cl.$^6$ ............... A61K 31/495; A61K 31/435; A61K 31/535; A61K 31/415

[52] U.S. Cl. ............ 514/212; 514/235.8; 514/252; 514/326; 514/392

[58] Field of Search ............... 514/212, 235.8, 514/252, 326, 392

[56] References Cited

U.S. PATENT DOCUMENTS 4,044,021  8/1977  Hanifin, Jr. et al. .............. 548/312
5,869,481  2/1999  Lankau et al. ..................... 514/212

FOREIGN PATENT DOCUMENTS 195 32 668  3/1997  Germany.

OTHER PUBLICATIONS

E. Siegel et al.: The Antiepileptic Drug AWD 131–138 Stimulates Different Recombinant Isoforms of the Rat GABA, etc., Neurosci.Ltr. (1998), 245(2), pp. 85–88.

A. Rostock et al.: AWD 131–138 as Anxiolytic Anticonvulsant, Durgs Future (1998), 23(3), pp. 253–255.

*Primary Examiner*—Keith D. MacMillan
*Attorney, Agent, or Firm*—Schweitzer Cornman Gross & Bondell LLP

[57] ABSTRACT

A process for the treatment of anxiety and tension, which comprises administering to a patient in need therefor an anxiolytically effective amount of a compound of the formula

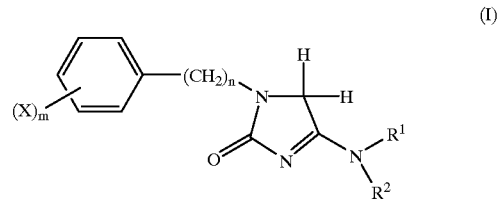

(I)

wherein X is hydrogen, a $C_{1-4}$ alkyl, $C_{1-4}$ alkoxy, trifluoromethyl residue, or halogen; $R^1$ and $R^2$ are independently of each other a $C_{1-4}$ alkyl, cycloalkyl, $C_{2-4}$ hydroxyalkyl, or heteroalkyl residue, or $R^1$ and $R^2$ together form a $C_{2-6}$ alkylene residue in which one —$CH_2$— group can be replaced by oxygen, nitrogen or sulfur; n is 0 or 1, and m is 0 or a cardinal number from 1–5, or a pharmaceutically acceptable salt of the compound.

3 Claims, 4 Drawing Sheets

| 48 | 100 | 200 | compd. Example 1 |
| 0.3 | 0.67 | 1.33 | diazepam |
| 0.06 | 0.12 | 0.24 | clonazepam |

FOR A PROCESS FOR TREATMENT OF ANXIETY AND TENSION

FIELD OF THE INVENTION

The invention relates to a process for treating anxiety and tension including epileptic disorders by the administration of 1-ar(alk)yl-imidazolin-2 one of formula (I) or their pharmaceutically acceptable salts.

BACKGROUND

Anxiety and tension of differing cause and intensity cannot be satisfactorily treated even today in all cases. Since approximately 1960, benzodiazepine derivatives have been employed as a matter of priority for the treatment of anxiety and tension. Substances having such a profile in general have a calming and emotion-damping action. These medicaments are a great help in the short term, but even in therapeutic doses side effects such as sedation, drowsiness and decreased responsiveness occur.

There can be a negative effect on mental processes due to sedation. Partly, ataxia and coordination disorders are to be observed, which affect the functional capacity. On continuous use, these benzodiazopine compounds lead to habituation effects, so-called tolerance. The efficacy of the preparation becomes lower and the dose has to be increased. A psychological dependence, moreover even a physiological dependence, can develop. Complicated withdrawal phenomena therefore occur in withdrawal trials.

The most important representatives of the anxiolytics on the market are the active compounds diazepam, clonazepam and medazepam. Plasma concentrations of 300 to 400 ng/ml are necessary to achieve an anxiolytic action of diazepam. The side effects mentioned, such as sedation and psychomotor disorders, which are manifested in daytime sedation, drowsiness and restricted attentiveness and responsiveness however, also occur, at the same concentrations. Severe "hangover" effects can occur, which are likewise associated with drowsiness, impairment of intellectual and motor capacities, and prolonged reaction time. The anxiolytic action of clonazepam is masked by sedating or hypnotic action. High doses of medazepam are also associated with hypnotic, muscle-relaxing phenomena.

All three anxiolytics potentiate the action of numerous centrally active pharmaceuticals and of alcohol. In this case, after administration of the individual substance seffects can occur which are barely noticeable.

Until now, there has been no success in achieving a satisfactory therapeutic standard in the case of relatively long-lasting anxiety states. A therapy-outlasting action of anxiolytic medicaments is presently also not adequately guaranteed.

SUMMARY OF THE INVENTION

The object of the present invention is to provide a process for the treatment of anxiety and tension with a great therapeutic breadth.

It has been surprisingly found that compounds of formula (I) have been found to have significant anxiolytic action without sedating.

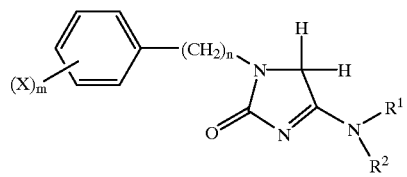

wherein
X is hydrogen, a $C_{1-4}$ alkyl, $C_{1-4}$ alkoxy, trifluoromethyl, or halogen residue;

$R^1$ and $R^2$ are independently of each other a $C_{1-4}$ alkyl, cycloalkyl, $C_{2-4}$ hydroxyalkyl, or heteroalkyl residue, or $R^1$ and $R^2$ together form a $C_{2-6}$ alkylene residue in which one —$CH_2$— group can be replaced by oxygen, nitrogen or sulfur;

n is 0 or 1, and m is 0 or a cardinal number from 1–5, or a pharmaceutically acceptable salt of the compound of formula (I).

The number of —$CH_2$— groups is either 0 as in the case of the 1-arylimidazolin-2-ones, or 1 as in the case of the 1-aralkylimidazolin-2-ones.

Examples of compounds of formula (I) include:

1-phenyl-4-morpholinoimidazolin-2-one,
1-(4-methoxy)-4-piperidinoimidazolin-2-one,
1-(4-chlorophenyl)-4-morpholinoimidazolin-2-one,
1-(4-chlorophenyl)-4-piperidinoimidazolin-2-one,
1-(4-chlorophenyl)-4-dimethylaminoimidazolin-2-one,
1-(4-bromopheny)-4-morpholinolmidazolin-2-one,
1-(3-chlorophenyl)-4-morpholinoimidazolin-2-one,
1-(4-chlorophenyl)-4-morpholinoimidazolin-2-one,
1-(4-chlorophenyl)-4-hexamethyleneiminoimidazolin-2-one,
1-(4-methylphenyl)-4-morpholinoimidazolin-2-one,
1-(4-chlorophenyl)-4-(cyclohexylmethylamino) imidazoline-2-one,
1-(4-fluorophenyl)-4-morpholinoimidazolin-2-one, and
1-benzyl-4-morpholinoimidazolin-2-one.

The compounds of formula (I) are known from U.S. application Ser. No. 08/708,665 for use as anticonvulsives, such as for the treatment of epilepsy. It has now be surprisingly found that those compounds also have an anxiolytitic effect, in that they are useful for the treatment of anxiety and tension.

BRIEF DESCRIPTION OF THE DRAWING

The present invention is explained in greater detail, by reference being had to the drawing, wherein.

DETAILED DISCLOSURE

A number of tests were carried out to determine the anxiolytic properties of compounds of formula (I). These animals were exposed to different conflict situations and, for example the effect of the compound 1-(4-chlorophenyl)-4-morpholinoimidazolin-2-one (Example 1) was determined.

Accordingly, the Vogel conflict test was employed to determine the inhibition of anxiety. In this model, continuous access to drinking water is withheld from rats for a certain lenght of time. After this period, free access is given to drinking water, but is coupled with a mild electrical stimulation. The conflict for the animals is between accepting the electrical stimulation of going without a drink.

Figure 1:
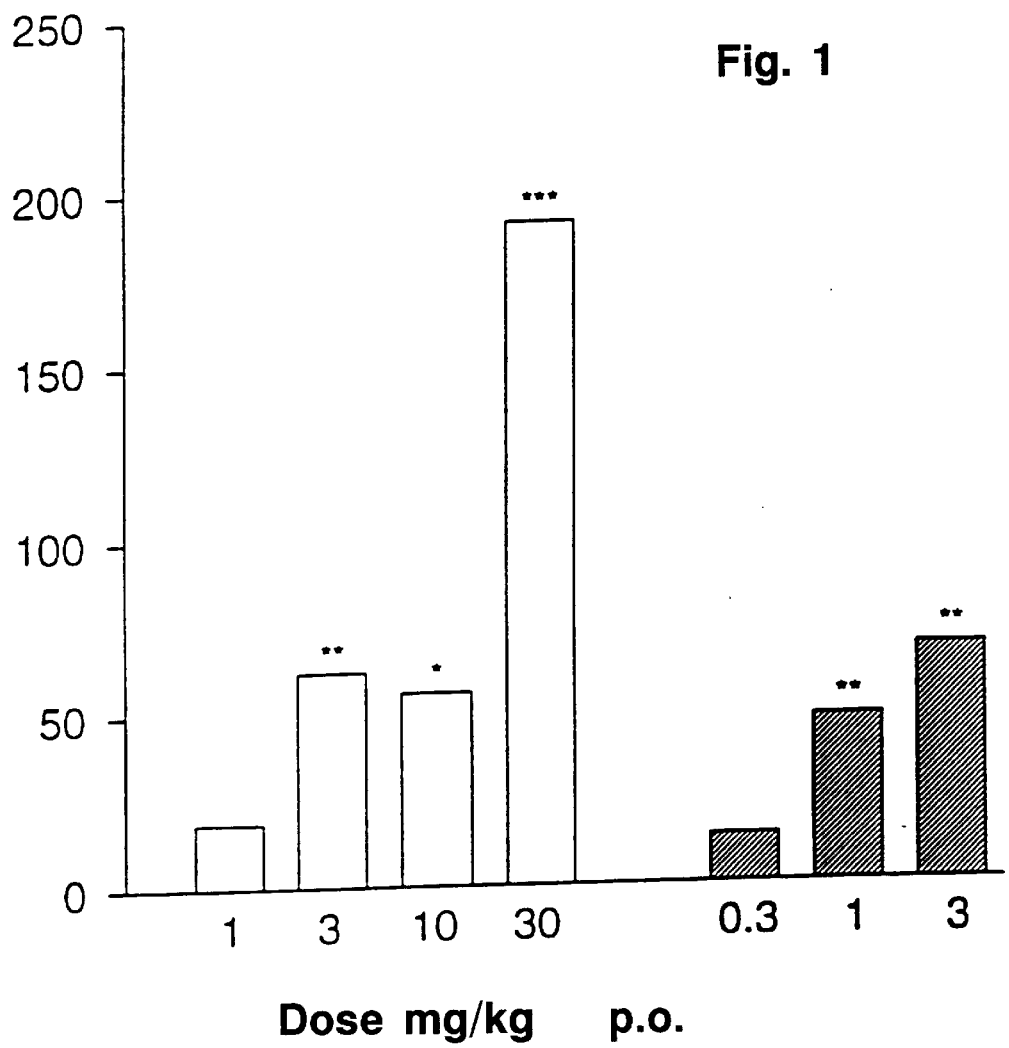
FIG. 1 is a diagram showing the number of impulses over the control (%)

The reactions to a conflict situation of this type are similar to the secondary phenomenon of anxiety in man. Avoidance reactions result, and these can be suppressed by anxiolytic substances. The number of tolerated current pulses of the animals treated with the test substance is assessed as a measure of the anxiolytic action in comparison to the controls. The experimental results obtained are graphically shown in FIG. 1.

TABLE 1

Anxiolytic action of substances in the Vogel conflict test in rat $X + SEM$; *p 0.05, **p 0.01

| Substance | mg/kg p.o. Dosage | Impulses | Changed Number of Impulses to the Control in |
|---|---|---|---|
| Control | — | 51.4 ± 7.73 | |
| Example | 1 | 61.3 ± 8.72 | 19.3 |
| | 3 | 83.2 ± 7.19** | 61.9 |
| | 10 | 80.1 ± 9.23** | 55.8 |
| Control | — | 39.6 ± 7.20 | |
| | 30 | 126.0 ± 15.7** | 218.0 |
| | — | 62.3 ± 7.07 | |
| | 0.1 | 58.4 ± 6.47 | −6.3 |
| Control | 0.3 | 70.9 ± 6.85 | 13.8 |
| Diazepam | 1.0 | 92.1 ± 3.22** | 47.8 |
| | 3.0 | 104.4 ± 11.9** | 67.6 |
| Control | — | 63.9 ± 6.63 | |
| Clonazepam | 0.1 | 77.7 ± 8.54 | 21.6 |
| | 0.3 | 81.8 ± 7.81 | 28.0 |
| | 1.0 | 110.3 ± 13.5* | 72.6 |
| Control | — | 54.6 ± 7.89 | |
| Medazepam | 0.3 | 54.8 ± 8.85 | 0.4 |
| | 1.0 | 71.3 ± 10.0 | 30.6 |
| | 3.0 | 42.7 ± 4.54 | −21.8 |

Anxiolytic action was detected for the compound of Example 1, even at a dose of 3 mg/kg p.o. which is not increased upon increasing the dose to 10 mg/kg p.o. After increasing the dose to 30 mg/kg p.o., it was possible to measure a potentiation of action. Equieffective doses of diazepam and clonazepam are 1 to 3 mg/kg p.o. and 1 mg/kg p.o. For medazepam it was not possible to detect any activity in the dose range from 0.3 to 3 mg/kg p.o.

Untreated animals drink significantly less, which means they are more anxious than animals which are treated with anxiety-inhibiting substances. The compound used in Example 1 from the dose of 3 mg/kg orally increases the number of electrical stimulations that are significantly tolerated. This effect confirms the good anxiolytic action of the compounds of formula (I).

It is therefore to be expected that the compounds of formula (I) cause an inhibition of anxiety, particularly in conflict situations.

Investigation of the Inhibition of Anxiety in the Elevated Maze

Figure 2:
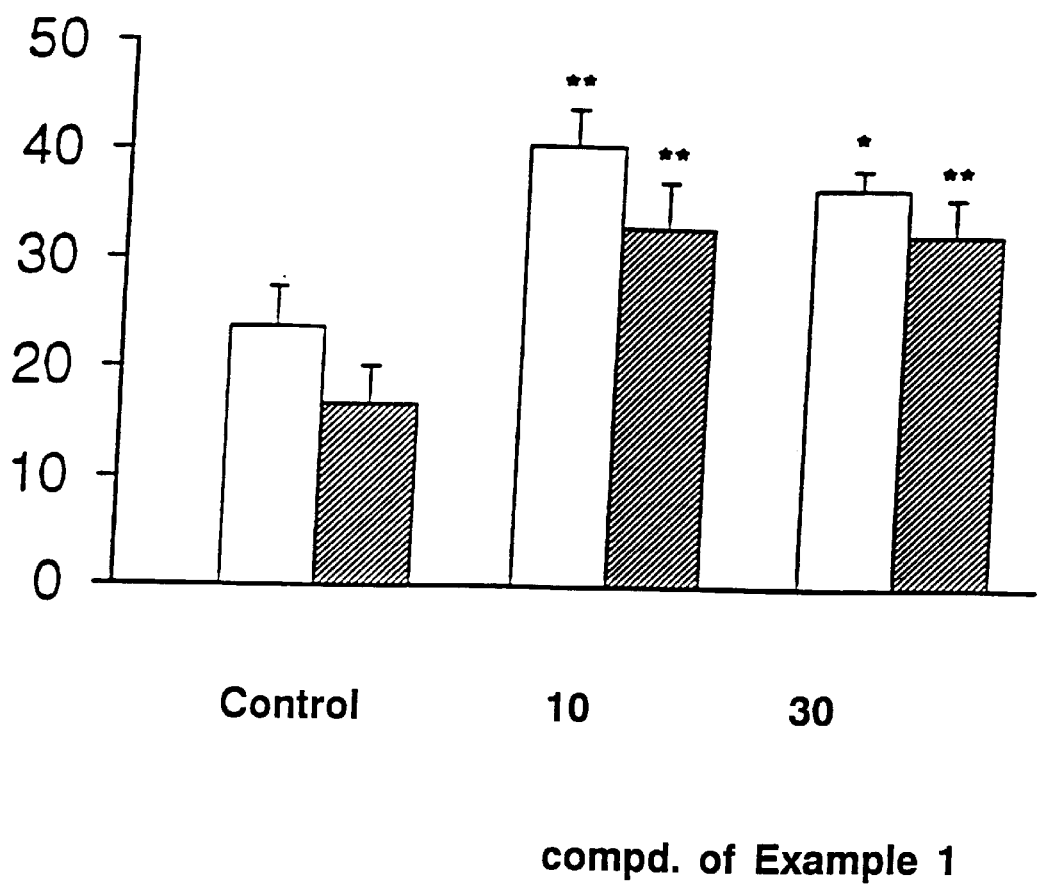
FIG. 2 is a diagram showing the relative i.p administered dosage effect over the control.

In this investigational model, rats are placed in an elevated maze with open and closed arms (see Pellow, S. et al.: Validation of Open: Closed Arm Entries in an Elevated Plus-Maze as a Measure of Anxiety in Rats; J. of Neuroscience Methods 14: 149–167, 1985; and Hogg, S.: A Review of the Validity and Variability of the Elevated Plus-Maze as an Animal Model of Anxiety; Pharmacology Biochemistry and Behavior: 21–30, 1996). Untreated animals repeatedly attempt the closed passages. The inhibition of anxiety is measured by the number of entries into the open arms and by the length of stay in the open arms as a percentage of the total entries or of the total length of stay. Treatments with the compound of Example 1, of formula (I) increase the entries and the length of stay in the open arms as a percentage, as can be seen from FIG. 2, p 0.05,** p 0.01 in comparison to the control. The proportion of the entries into the open arms and the time of stay in the open arms is significantly increased after intraperitoneal administration of 10 or 30 mg/kg of the compound of Example 1.

In the pharmacological experiment, the compounds of formula (I) showed a strong separation between the anxiolytic action and the sedating effects. It is evident from the "therapeutic breadth" results shown in FIG. 3 that, for example, the compound of Example 1 exhibits a significantly lower sedation in rats compared with the diazepam and clonazepam controls.

Figure 3:
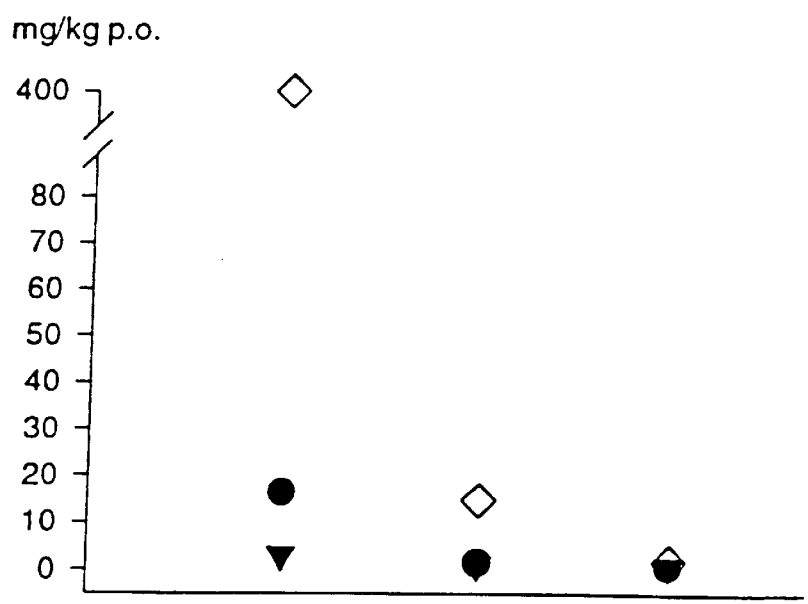
FIG. 3 is a diagrammatic comparison of the p.o. dosage effects over controls.

The centrally sedating action of the compounds of formula (I) was investigated in mice. The animals were administered an amount of alcohol which did not cause any mice to lie on their sides. It was checked to what extent the hypnotic effect of alcohol is potentiated and the animals can be induced to lie on their sides by additional administration of compounds of formula (I). Doses, for example, of the compound of Example 1 which are 15 to 66-fold the anxiolytic dose induce only a low and non-dose-pendent potentiation of the action of alcohol. Diazepam and clonazepam, in contrast, were investigated in the anxiolytic dose range. For both standard compounds, it was possible to measure a strong and dose-dependent potentiation of the action of alcohol (FIG. 3).

The compounds of formula (I) have a very low neurotoxicity compared with the comparison substances diazepam and clonazepam.

The minimum neurotoxic dose of the compound of Example 1 was determined in the rotorod test as 998 mg/kg p.o.

Figure 4:
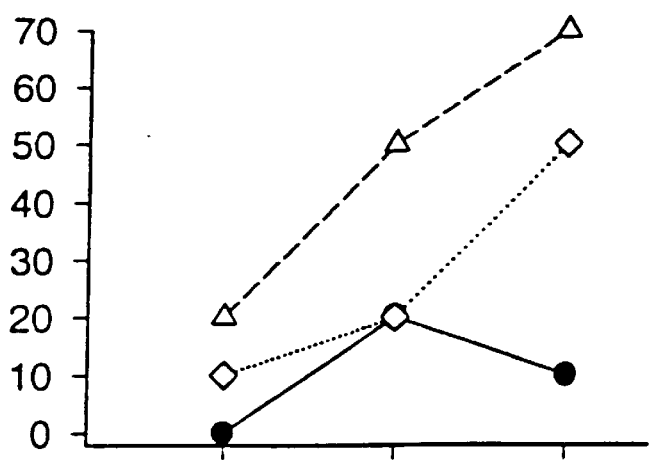
FIG. 4 is a diagrammatic comparison on subhypnotic doses of alcohol.

The therapeutic index, calculated as the quotient of the minimum neurotoxic dose in the rotorod test and the anxiolytic dose, is very high with the value 333 and points to a great therapeutic breadth, as can be seen from FIG. 4.

The therapeutic breadth of a substance as an important pharmacological characteristic quantity is a measure of the safety between therapeutic and toxic action. It was therefore all the more surprising that compounds of formula (I) have a significantly higher therapeutic breadth compared with anxiolytically active substances on the market. As a result, the treatment of patients with anxiety and tension states, in particular even over a relatively long period of time, is markedly improved.

The compounds of formula (I) of their pharmaceutically acceptable salts can be converted in a known manner into pharmaceutical formulations such as tablets, capsules, coated tablets, granules, emulsions, suspensions or solutions.

The customary pharmaceutical excipients and auxiliaries can be used for the production of these preparations. A suitable daily dose can be determined by routine dosage ranging and would be suitably between about 0.01 and about 1.5 mg kg body weight.

We claim:

1. A process for the treatment of anxiety and tension, which comprises administering to a patient in need therefor an anxiolytically effective amount of a compound of the formula

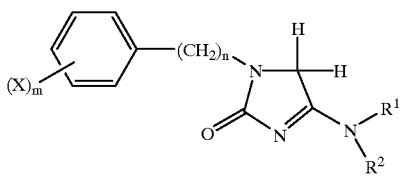

(I)

wherein
- X is hydrogen, a $C_{1-4}$ alkyl, $C_{1-4}$ alkoxy, trifluoromethyl residue, or halogen;
- $R^1$ and $R^2$ are independently of each other a $C_{1-4}$ alkyl, cycloalkyl, $C_{2-4}$ hydroxyalkyl, or heteroalkyl residue, or
- $R^1$ and $R^2$ together form a $C_{2-6}$ alkylene residue in which one —$CH_2$— group can be replaced by oxygen, nitrogen or sulfur;
- n is 0 or 1, and m is 0 or a cardinal number from 1–5, or a pharmaceutically acceptable salt of the compound of formula (I).

2. The process of claim 1, wherein the anxiety is a conflict-related anxiety.

3. The process of claim 1, wherein said compound is:
1-phenyl-4-morpholinoimidazolin-2-one,
1-(4-methoxy)-4-piperidinoimidazolin-2-one,
1-(4-chlorophenyl)-4-morpholinoimidazolin-2-one,
1-(4-chlorophenyl)-4-piperidinoimidazolin-2-one,
1-(4-chlorophenyl)-4-dimethylaminoimidazolin-2-one,
1-(4-bromopheny)-4-morpholinoimidazolin-2-one,
1-(3-chlorophenyl)-4-morpholinoimidazolin-2-one,
1-(4-chlorophenyl)-4-morpholinoimidazolin-2-one,
1-(4-chlorophenyl)-4-hexamethyleneiminoimidazolin-2-one,
1-(4-methylphenyl)-4-morpholinoimidazolin-2-one,
1-(4-chlorophenyl)-4-(cyclohexylmethylamino)imidazoline-s-one,
1-(4-fluorophenyl)-4-morpholinoimidazolin-2-one, and
1-benzyl-4-morpholinoimidazolin-2-one.

* * * * *

UNITED STATES PATENT AND TRADEMARK OFFICE
CERTIFICATE OF CORRECTION

PATENT NO. : 5,994,347 Page 1 of 1
APPLICATION NO. : 09/079802
DATED : November 30, 1999
INVENTOR(S) : Rostock et al.

It is certified that error appears in the above-identified patent and that said Letters Patent is hereby corrected as shown below:

On the cover page, item 54 and col. 1, in line 1 of the title, delete "FOR A".

Column 2, line 30, replace "1-(4-methoxy)-4- [..]" with -- 1-(4-methoxyphenyl)-4- [..] --.

Column 2, line 36, delete "1-(4-chlorphenyl)-4-morpholinoimidazolin-2-one,".

Claim 3, column 6, line 7, replace "1-(4-methoxy)-4- [..]" with
-- 1-(4-methoxyphenyl)-4- [..] -- .

Claim 3, column 6, line 13, delete "1-(4-chlorphenyl)-4-morpholinoimidazolin-2-one,".

Signed and Sealed this

Ninth Day of February, 2010

David J. Kappos
*Director of the United States Patent and Trademark Office*